United States Patent [19]

Thiruvengadam et al.

[11] Patent Number: 5,306,817
[45] Date of Patent: Apr. 26, 1994

[54] PROCESS FOR THE STEREOSPECIFIC SYNTHESIS OF AZETIDINONES

[75] Inventors: Tiruvettipuram K. Thiruvengadam, Edison; Chou-Hong Tann, Berkeley Heights; Junning Lee, Springfield; Timothy McAllister, Fords; Anantha Sudhakar, East Brunswick, all of N.J.

[73] Assignee: Schering Corporation, Kenilworth, N.J.

[21] Appl. No.: 962,768

[22] Filed: Oct. 19, 1992

Related U.S. Application Data

[63] Continuation-in-part of PCT/US92/05972, Jul. 21, 1992, which is a continuation-in-part of Ser. No. 734,652, Jul. 23, 1991, abandoned, and a continuation-in-part of Ser. No. 734,426, Jul. 23, 1991, abandoned.

[51] Int. Cl.$^5$ ..................... C07D 205/08; C07B 53/00
[52] U.S. Cl. ..................................... 540/200; 540/362
[58] Field of Search ............................... 540/200, 362

[56] References Cited

U.S. PATENT DOCUMENTS

| | | | |
|---|---|---|---|
| 4,235,913 | 11/1980 | Johnson | 546/269 |
| 4,405,516 | 9/1983 | Hunkeler | 540/487 |
| 4,745,201 | 5/1988 | Hsiao et al. | 548/110 |
| 4,774,245 | 9/1988 | Watjen | 544/346 |
| 4,845,229 | 7/1989 | Hsiao et al. | 548/110 |
| 4,870,169 | 9/1989 | Evans et al. | 540/229 |

OTHER PUBLICATIONS

Thompson, Tet. Letters 32, 3337-3340 (1991).
Sowin, J. Org. Chem 53, 4154 (1988).
Evans et al, Tetrahedron Letters, 27(27), 3119-3122 (1986).
Gage et al, Organic Synthesis, 68, 77-91 (1990).
Jung et al, Tetrahedron Letters, 26(8), 977-980 (1985).
Mattingly et al, J. Amer. Chem. Soc., 101, 3983-3985 (1979).
Miller et al, J. Amer. Chem. Soc., 102, 7026-7032 (1980).
Hsaio et al, Tetrahedron Letters, 26(40), 4855-4858 (1985).
Townsend et al, Tetrahedron Letters, 23(47), 4859-4862 (1982).
Hsiao et al, J. Org. Chem., 52, 2201-2206 (1987).
Evans et al, J. Amer. Chem. Soc., 103, 2127-2129 (1981).
Roberts, "Basic Principles of Organic Chemistry" p. 562 (1985).
Kita, et al., J. Chem. Soc. Chem. Comm., 727-729 (1990).
Annunziata et al, Tetrahedron Letters, 33(8), 1113-1116 (1992).
Corey et al, Tetrahedron Letters, 32(39), 5287-5290 (1991).

Primary Examiner—Mark L. Berch
Attorney, Agent, or Firm—Paul A. Thompson; Anita W. Magatti

[57] ABSTRACT

This invention provides an improved process for producing azetidinones. More particularly, this invention provides the steps of producing an trans-azetidinone represented by the formula

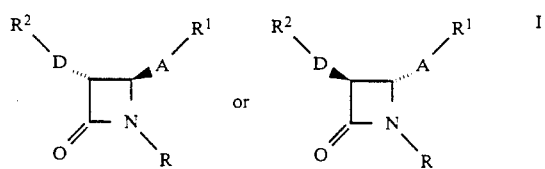

from a carboxylic acid $R^2$-D-$CH_2$-COOH, an aldehyde $R^1$-A-CHO and an amine $RNH_2$, by the steps of: (a1) converting a carboxylic acid to the corresponding acid chloride; (b1) deprotonating a chiral oxazolidinone and treating the resulting anion with the product of step (a1); (c1) enolizing the product of step (b1) and condensing with the aldehyde; (d1) hydrolyzing the product of step (c1); (e1) condensing the product of step (d1) with the amine; and (f1) cyclizing the product of step (e1).

Alternatively, the process comprises (a2) enolizing the product of step (b1) and condensing, in the presence of a Lewis acid, with a Schiff's base prepared from the aldehyde and the amine; and (b2) cyclizing the product of step (a2).

7 Claims, No Drawings

PROCESS FOR THE STEREOSPECIFIC SYNTHESIS OF AZETIDINONES

BACKGROUND

This application is a continuation-in-part of PCT International Application No. PCT/US92/05972, filed Jul. 21, 1992, which in turn is a continuation-in-part of U.S. Ser. No. 07/734,652, filed Jul. 23, 1991 and U.S. Ser. No. 07/734,426, filed Jul. 23, 1991 both abandoned.

This invention relates to an improved stereospecific process for producing azetidinones useful as hypocholesterolemic agents and as intermediates for the synthesis of penems.

In a process heretofore utilized to prepare azetidinones, a boron enolate of a butyrimide, prepared from butyric acid and 4(R),5(S)-4-methyl-5-phenyloxazolidinone, and 3-methoxymethylphenylacetaldehyde are reacted to form a compound of formula

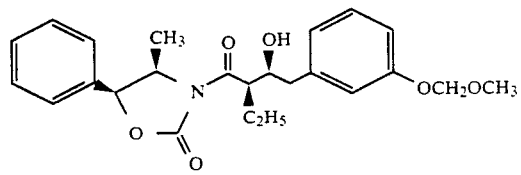

as disclosed in Evans, et al, *Tetrahedron Letters*, 27 (27), 3119–3122 (1986). The chiral oxazolidinone is displaced by reacting with methoxyamine hydrochloride and trimethylaluminum to form a β-hydroxyhydroxamide. The β-hydroxy group is converted to a mesylate, which is cyclized by treatment with potassium carbonate to form an N-methoxyazetidinone. Finally, the N-methoxyazetidinone is reduced by dissolving metal reduction, using lithium and ammonia, to form an azetidinone of formula

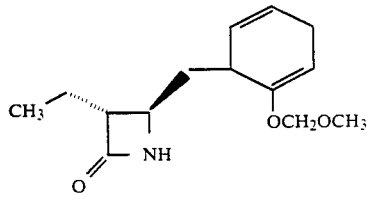

Gage, et al, *Organic Synthesis*, 68, 77–91 (1989) discloses a process for preparing (2S*,3S*)-3-hydroxy-3-phenyl-2-methylpropanoic acid from a chiral oxazolidinone. The process is shown in Reaction Scheme I.

Reaction Scheme I

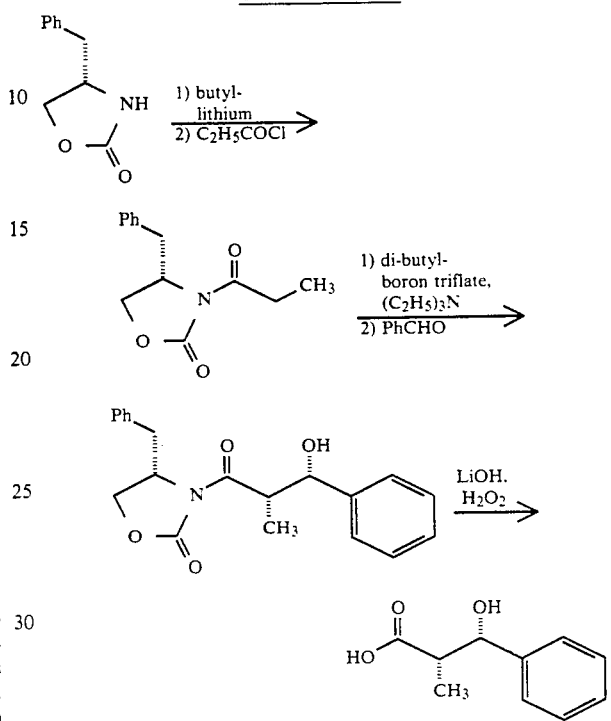

Jung, et al, *Tetrahedron Letters*, 26 (8), 977–980 (1985), disclose a process for converting a β-hydroxycarboxylic acid to an N-hydroxy-β-lactam. The process is shown in Reaction Scheme II. In addition, Jung, et al incorporate by reference Mattingly, et al, *J. Amer. Chem. Soc.*, 101, 3983 (1979) and Miller, et al, *J. Amer. Chem. Soc.*, 102, 7026 (1980) which disclose methods for the reductive cleavage of N-hydroxy-β-lactams to form β-lactams.

Reaction Scheme II:

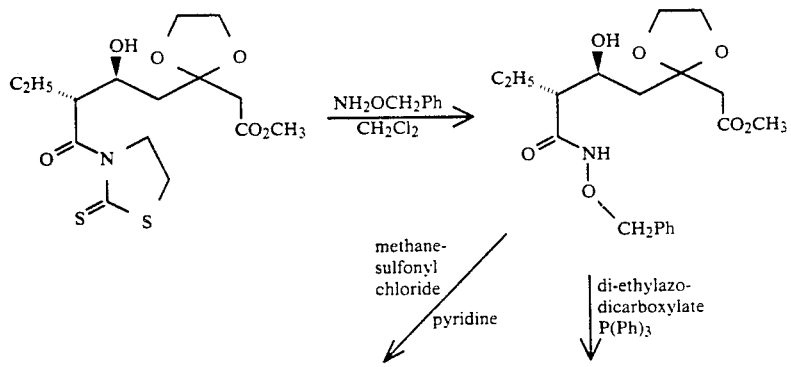

Reaction Scheme II:

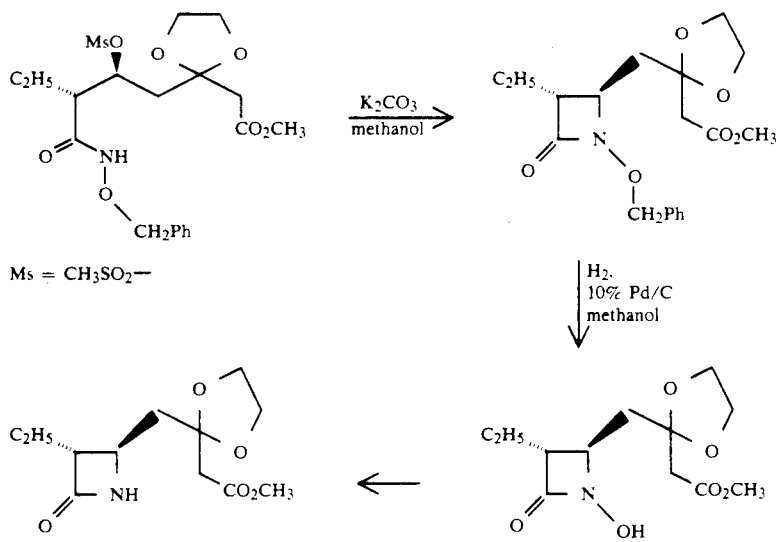

Ms = CH₃SO₂—

The Evans, et al, process suffers from several shortcomings. In particular, the process has not proved applicable to all azetidinones of formula I, below. With some substrates, the use of trimethylaluminum to form the β-hydroxy-hydroxamide results in a low reaction yield and requires laborious purification procedures to isolate the product. In addition, where the Evans, et al. process is used for preparing compounds of formula I, wherein —A—R¹ (as defined below) is capable of stabilizing a carbo-cation, e.g. wherein —A—R¹ is phenyl, naphthyl or W-substituted phenyl or naphthyl, the mesylate cyclization step is accompanied by epimerization.

The process of Gage, et al, provides an efficient route to β-hydroxy-carboxylic acids. However, the Jung, et al, process for converting such compounds to β-lactams suffers from a lack of generality, giving variable yields of product in the cyclization step, depending upon the substrate employed.

SUMMARY OF THE INVENTION

This invention provides an improved process for producing azetidinones useful as intermediates in the synthesis of penems. Penems are a known group of antibacterials. In addition, azetidinones prepared via this process are useful as hypocholesterolemic agents, as disclosed in co-owned, copending PCT International Application No. PCT/US92/05972. More particularly, this invention provides the steps of producing an azetidinone represented by the formula I

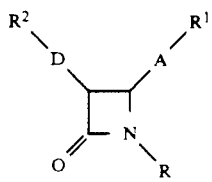

wherein

R is phenyl, W-substituted phenyl, naphthyl, W-substituted naphthyl, benzodioxolyl, heteroaryl, W-substituted heteroaryl, benzofused heteroaryl and W-substituted benzofused heteroaryl, wherein heteroaryl is selected from the group consisting of pyrrolyl, pyridinyl, pyrimidinyl, pyrazinyl, triazinyl, imidazolyl, thiazolyl, pyrazolyl, thienyl, oxazolyl and furanyl, and for nitrogen-containing heteroaryls, the N-oxides thereof;

$R^1$ and $R^2$ are independently selected from H or R;

W is 1 to 3 substituents independently selected from the group consisting of lower alkyl, hydroxy lower alkyl, lower alkoxy, alkoxyalkyl, alkoxyalkoxy, alkoxycarbonylalkoxy, (lower alkoxyimino)lower alkyl, lower alkanedioyl, lower alkyl lower alkanedioyl, allyloxy, —CF₃, —OCF₃, benzyl, R³-benzyl, benzyloxy, R³-benzyloxy, phenoxy, R³-phenoxy, dioxolanyl, NO₂, —NR⁴R⁵, NR⁴R⁵(lower alkyl)-, NR⁴R⁵(lower alkoxy)-, OH, halogeno, —NHC(O)OR⁶, —NHC(O)R⁶, $R^7O_2SNH—$, $(R^7O_2S)_2N—$, —S(O)₂NH₂, —S(O)₀₋₂R⁴, tert-butyldimethylsilyloxymethyl, —C(O)R⁸,

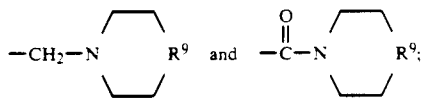

A and D are independently a bond; C₃-C₆ cycloalkylene; C₁-C₁₀ alkylene; C₁-C₁₀ alkenylene; C₁-C₁₀ alkynylene; an alkylene, alkenylene or alkynylene chain as defined substituted by one or more substituents independently selected from the group consisting of phenyl, W-substituted phenyl, heteroaryl and W-substituted heteroaryl, wherein heteroaryl is as defined above; an alkylene, alkenylene or alkynylene chain as defined interrupted by one or more groups independently selected from the group consisting of —O—, —S—, —SO—, —SO₂—, —NR₈, —C(O)—, C₃-C₆ cycloalkylene, phenylene, W-substituted phenylene, heteroarylene and W-substituted heteroarylene; or an interrupted alkylene, alkenylene or alkynylene chain as defined substituted by one or more substituents independently selected from the group consisting of phenyl, W-substituted phenyl, heteroaryl and W-substituted heteroaryl; or R²-D is selected from the group consisting of halogeno, OH, lower alkoxy, —OC(O)R⁶, —NR⁴R⁵, —SH and —S(lower alkyl);

$R^3$ is 1-3 groups independently selected from the group consisting of lower alkyl, lower alkoxy, —COOH, $NO_2$, —$NR^4R^5$, OH or halogeno;

$R^4$ and $R^5$ are independently selected from H and lower alkyl;

$R^6$ is lower alkyl, phenyl, $R^3$-phenyl, benzyl or $R^3$-benzyl;

$R^7$ is OH, lower alkyl, phenyl, benzyl, $R^3$-phenyl or $R^3$-benzyl;

$R^8$ is H, OH, alkoxy, phenoxy, benzyloxy,

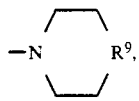

—$NR^4R^5$, lower alkyl, phenyl or $R^3$-phenyl;

$R^9$ is —O—, —$CH_2$—, —NH— or —N(lower alkyl)-;

$R^{10}$ is H, lower alkyl, phenyl lower alkyl or —C(O)$R^{11}$;

$R^{11}$ is H, lower alkyl, phenyl or phenyl lower alkyl;

provided that when A is a bond, $R^1$ is not H, and provided that when $R^1$ is W-substituted phenyl, W is not p-halogeno; wherein the substitutents $R^2$-D- and $R^1$-A- have trans relative stereochemistry, from a hydroxyamide of the formula

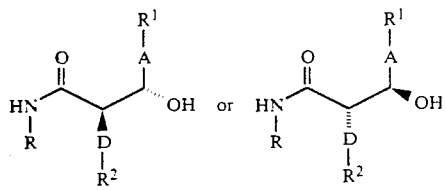

wherein D, A, $R^1$, $R^2$ and R are as defined above, by cyclizing the hydroxyamide, and wherein the hydroxyamide is prepared from a carboxylic acid $R^2$-D-$CH_2COOH$, an aldehyde $R^1$-A-CHO and an amine $RNH_2$, wherein D, A, $R^1$, $R^2$ and R are as defined above, in a process utilizing as a chiral auxiliary a compound of the formula

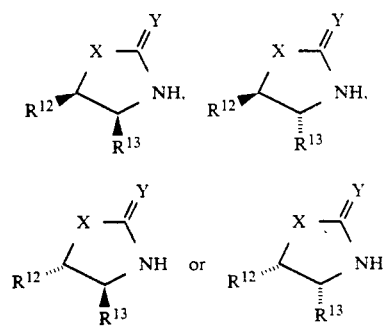

wherein: X and Y are independently O or S, and $R^{12}$ and $R^{13}$ are independently selected from the group consisting of $C_1$-$C_6$ alkyl, phenyl, naphthyl, W-substituted phenyl, W-substituted naphthyl, lower alkoxycarbonyl and benzyl; or wherein one of $R^{12}$ or $R^{13}$ is as defined above and the other is hydrogen.

This process, designated Method A, for producing compounds of formula I, wherein $R^2$-D and $R^1$-A have trans relative stereochemistry, comprises the steps:

(a) reacting a carboxylic acid of the formula $R^2$-D-$CH_2COOH$, wherein $R^2$ and D are as defined above, with a chlorinating agent;

(b) deprotonating the chiral auxillary, as described above, with a strong base or a tertiary amine base and treating the resulting anion with the product of step (a);

(c) enolizing the product of step (b) with either:
  (i) a dialkylboron triflate and a tertiary amine base; or
  (ii) $TiCl_4$ and a tertiary amine base selected from: tetramethylethylenediamine (TMEDA); triethylamine; or a mixture of TMEDA and triethylamine;

then condensing with an aldehyde of the formula $R^1$-A-CHO, wherein $R^1$ and A are as defined above;

(d) hydrolyzing the product of step (c) with a base and hydrogen peroxide;

(e) condensing the product of step (d) with an amine of the formula $RNH_2$, wherein R is as defined above, by treating with a dehydrative coupling agent, optionally adding an activating agent;

(f) cyclizing the product of step (e) by reacting the product of step (e) with:
  (i) a dialkylazodicarboxylate and a trialkylphosphine; or
  (ii) a di- or tri-chlorobenzoyl chloride, an aqueous solution of a base and a phase transfer catalyst; or
  (iii) a di- or tri-chlorobenzoyl chloride, an aqueous solution of a base and a phase transfer catalyst, isolating the resulting di- or tri-chlorobenzoate intermediate, then treating the intermediate with an aqueous solution of a base and a phase transfer catalyst; or
  (iv) a dialkylchlorophosphate and either a metal hydride, or an aqueous solution of a base and a phase transfer catalyst; or
  (v) a di- or tri-chlorobenzoyl chloride and a metal hydride.

In another embodiment, the process of this invention, designated Method B, provides the steps of producing a β-lactam of formula I, wherein $R^2$-D and $R^1$-A have trans relative stereochemistry, from a β-aminoamide derivative of the formula

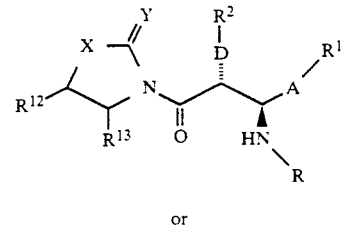

or

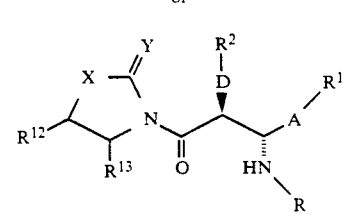

by cyclizing the β-aminoamide, wherein the β-aminoamide is prepared from a carboxylic acid $R^2$—D—$CH_2COOH$, and an imine $R^1$—A—CH=N—R, wherein D, A, $R^1$, $R^2$ and R are as defined above, in a process utilizing as a chiral auxiliary a compound of the formula

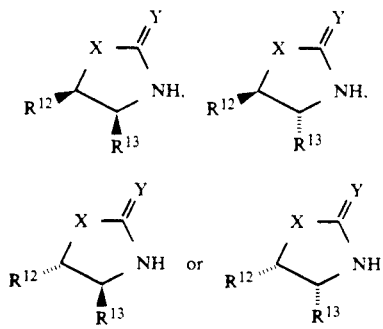

wherein X, Y, $R^{12}$ and $R^{13}$ are as defined above.

This process, designated Method B, for producing compounds of formula I, wherein $R^2$-D and $R^1$-A have trans relative stereochemistry, comprises the steps:

(a) enolizing the product of Method A, step (b) with a Lewis acid of the formula $Ti(Cl)_m(OR^{14})_n$, wherein $R^{14}$ is lower alkyl, m is 1, 2, 3 or 4, n is 0, 1, 2 or 3, and m+n=4, and a tertiary amine base, then condensing with an imine of the formula $R^1$—A—CH=N—R, wherein $R^1$, A and R are as defined above;

(b) cyclizing the product of step (a) by treating with a strong non-nucleophilic base.

DETAILED DESCRIPTION

As used herein, the term "lower alkyl" means straight or branched alkyl chains of 1 to 6 carbon atoms and "lower alkyoxy" similarly refers to alkoxy groups having 1 to 6 carbon atoms;

"Alkenyl" means straight or branched carbon chains having one or more double bonds in the chain, conjugated or unconjugated, and alkadienyl refers to chains having two double bonds in the chain; similarly, "alkynyl" means straight or branched carbon chains having one or more triple bonds in the chain.

Where an alkyl, alkenyl or alkynyl chain joins two other variables and is therefore bivalent, the terms alkylene, alkenylene and alkynylene are used.

"Cycloalkyl" means a saturated carbon ring of 3 to 6 carbon atoms, while "cycloalkylene" refers to a corresponding bivalent ring, wherein the points of attachment to other groups include all positional isomers.

"Halogeno" refers to fluorine, chlorine, bromine or iodine radicals.

"Heteroaryl" includes all positional isomers for a given heteroaryl group as defined above, for example 2-pyridyl, 3-pyridyl and 4-pyridyl. Benzofused heteroaryl refers to radicals formed by the bonding of a benzene radical to adjacent carbon atoms on a heteroaryl ring; examples are indolyl, quinolyl, quinazolinyl, quinoxalinyl, benzotriazolyl, indazolyl, benzoxazolyl, benzothienyl and benzofuranyl.

"Phenylene" means a bivalent phenyl group bound in an ortho, meta or para orientation and "heteroarylene" similarly means a bivalent heteroaryl group, including all positional isomers.

"(Lower alkoxyimino)lower alkyl" refers to the group ($C_1$-$C_6$ lower alkoxy)—N=CH-($C_1$-$C_5$ lower alkyl). "Lower alkanedioyl" means radicals of the formula —OC(O)$(CH_2)_{1-4}$C(O)OH, while "lower alkyl lower alkanedioyl" means radicals of the formula —OC(O)$(CH_2)_{1-4}$C(O)O-(lower alkyl).

$R^3$-benzyl and $R^3$-benzyloxy refer to benzyl and benzyloxy radicals which are substituted on the phenyl ring.

The carbon chains as defined in A and D, when substituted by optionally substituted phenyl or heteroaryl groups, may include independent substitution on different carbon atoms, di-substitution on one carbon atom, or both. One skilled in the art will recognize that the number of double or triple bonds present, the replacement of carbon atoms in the chain and the presence of substitutents on the carbon atoms in the chain are all dependent on the length of the chain: shorter carbon chains cannot accommodate as many double or triple bonds, carbon replacements or substituents as longer carbon chains can. In general, unsaturated carbon chains contain 1 to 4 double or triple bonds, conjugated or non-conjugated. Where carbon atoms are replaced, 1 to 4 replacement groups can be present. Similarly, when carbon atoms in the chain are substituted, 1 to 4 substituents can be present.

Examples of alkyl chains are methyl, ethyl, propyl, butyl and decyl.

Examples of unsaturated A and D groups are ethylene and acetylene.

Examples of A and D groups wherein the carbon atoms in the chain are replaced are —$CH_2CH_2O$—, —$OCH_2CH_2$—, —$CH_2O$—, —$CH_2CH_2CH_2O$—, —$CH_2$—O—$CH_2$—, —$CH_2CH_2$—O—$CH_2$, —$CH_2CH_2$—NH—, —$CH_2CH_2$—N($CH_3$)— and —O—$CH_2$-C(O)—NH—.

Compounds of formula I have at least two asymmetrical carbon atoms and therefore all isomers, including diastereomers and rotational isomers are contemplated as being part of this invention. The invention includes d and l isomers in both pure form and in admixture, including racemic mixtures. Isomers can be prepared using conventional techniques, either by reacting enantiomeric starting materials or by separating isomers of a compound of formula I or II.

Isomers may include geometric isomers, e.g. when A or D contains a double bond. All such isomers are contemplated for this invention.

The chiral auxiliary utilized is preferably an oxazolidinone, i.e., an auxiliary as defined above wherein X and Y are both O; and said chiral auxiliary is most preferably R-(+)-4-benzyloxazolidinone or S-4-phenyloxazolidinone.

"Suitable inert organic solvent" means any organic solvent or combination of solvents that is unreactive in the reaction being conducted and is a solvent for the reactants. Such solvents used in the various reactions of this invention are identified in the discussion of reaction schemes and in the examples. Typical suitable solvents are halogenated compounds such as chloroform or dichloromethane; heterocyclic compounds such as tetrahydrofuran (THF); dimethylformamide (DMF); dimethylsulfoxide (DMSO), lower alkanols (C1-C6 branched or straight chain alkanols) such as methanol; acetonitrile; and carbocyclic aromatics such as toluene.

"Tertiary amine base" means a trialkylamine, such as triethylamine, diisopropylethylamine (Hünig's base) or tetramethylethylenediamine (TMEDA), or a nitrogen containing heterocycle, such as pyridine.

"Base" means a metal hydroxide base such as lithium, sodium or potassium hydroxide.

"Strong base" means a non-aqueous base such as a metal hydride or an alkyllithium.

"Strong non-nucleophilic base" means a non-aqueous base which does not act as a nucleophile by virtue of its steric bulk, such as sodium bistrimethylsilylamide or lithium diisopropylamide, preferably sodium bistrimethylsilylamide.

"Halogeno" means a fluoro, chloro, bromo or iodo radical.

"Metal hydride" means a commercially available metal hydride such as lithium, sodium or potassium hydride.

"Alkyllithium" means an alkyllithium reagent such as n-butyllithium, s-butyllithium, t-butyllithium or methyllithium.

"Dehydrative coupling agent" means a carbodiimide such as 1-(3'-dimethylaminopropyl)-3-ethylcarbodiimide hydrochloride (DEC) or dicyclohexylcarbodiimide (DCC).

"Activating agent" means an agent used to facilitate the formation of amide bonds such as 1-hydroxybenzotriazole (HOBT) or N-hydroxysuccinimide.

"Halide salt" means a metal salt of a halogen such as sodium, lithium or potassium bromide.

"Lewis acid" means a Lewis acid of the formula $Ti(Cl)_m(OR^{14})_n$, wherein $R^{14}$, m and n are as defined above, preferably $TiCl_4$ or $TiCl(O\text{-}i\text{-propyl})_3$, most preferably $TiCl_4$.

"Phase transfer catalyst" means a cationic salt, such as a quaternary ammonium or phosphonium salt, preferably a quaternary ammonium salt, capable of complexing with and facilitating the transport of anions, such as hydroxide, between the aqueous phase and the organic phase of a biphasic mixture. Such catalysts can be utilized in either stoichiometric or catalytic, e.g. less than stoichiometric, quantities. Preferred phase transfer catalysts include benzyltriethylammonium chloride and tetra-n-butylammonium hydrogen sulfate.

In one aspect (Method A), the process of this invention comprises converting the product obtained by condensing a chiral imide with an aldehyde to a β-lactam according to Reaction Scheme A. The preferred stereoisomers are depicted for illustrative purposes in all reaction schemes which follow. Although the preferred stereochemistry of the reactants and intermediates in the process of this invention are as indicated in the various depicted structural formulas, it is to be understood that the process of this invention is operative for other stereoisomers and involves merely the selection of reactants having the desired stereochemical configuration and reaction conditions which result in the desired stereoisomers.

Reaction Scheme A

Step A1

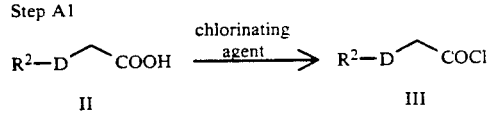

Step A2

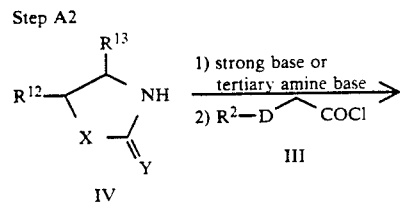

-continued
Reaction Scheme A

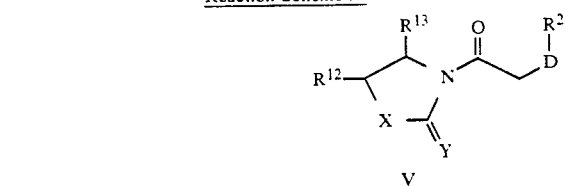

Step A3

V $\xrightarrow[\substack{(alkyl)_2BSO_3CF_3, \\ \text{tertiary amine base;} \\ \text{or} \\ TiCl_4, \text{ TMEDA (or TMEDA +} \\ \text{triethylamine})}]{R^1-A-CHO \quad VI}$

[Structure VII]

Step A4

VII $\xrightarrow{H_2O_2/\text{base}}$ [Structure VIII]

Step A5

VIII $\xrightarrow[\substack{\text{coupling agent} \\ \text{activating agent}}]{RNH_2 \quad IX}$ [Structure X]

Step A6

(i) P(alkyl)₃ + dialkylazodicarboxylate; or
(ii) di- or tri-chlorobenzoyl chloride, aqueous base, phase transfer reagent; or
(iii) dialkylchlorophosphate and either (a) metal hydride, or (b) aqueous base, phase transfer reagent; or
(iv) di- or tri-chlorobenzoyl chloride + alkali metal hydride X $\longrightarrow$ [Structure I]

In step A1 of Method A, the carboxylic acid II is treated with a chlorinating agent, e.g., thionyl chloride or oxalyl chloride, under a dry atmosphere, neat or in a suitable inert organic solvent, e.g., toluene, at 70° C. to produce compound III.

In step A2, chiral auxillary IV, preferably R-(+)-4-benzyloxazolidinone is converted to compound V in a two step reaction, first by deprotonating with a strong base, such as an alkyllithium, e.g., n-butyllithium, or a metal hydride, e.g., sodium hydride, or a tertiary amine base, such triethylamine, in a suitable anhydrous organic solvent, e.g., dry THF, under a dry, inert atmosphere, e.g., nitrogen, at about 0° C. to about −85° C., preferably about −78° C., over a period of about 30 to about 90 minutes, preferably about 60 minutes, and second by reacting the resulting anion, without isolation, with compound III in a suitable anhydrous organic solvent, e.g., dry THF, under a dry, inert atmosphere, e.g., nitrogen, at about −50° C. to about −85° C., preferably about −78° C., over a period of about 30 to about 60 minutes, preferably about 45 minutes, followed by continued reaction at about −10° C. to about 10° C., preferably about 0° C., for a period of about 30 to about 90 minutes, preferably about 60 minutes, then isolating the product, compound V, by extraction.

In step A3, compound V is treated with a dialkylboron triflate, e.g., di-n-butylboronitriflate (Bu$_2$BOSO$_2$CF$_3$), in a suitable inert organic solvent, e.g., CH$_2$Cl$_2$, under a dry, inert atmosphere, e.g., nitrogen, at about −60° C. to about 10° C., preferably about −10° C. to about 0° C. for a period of about 10 minutes. A tertiary amine base, e.g., diisopropylethylamine, is added at about −10° C. to about 0° C., preferably about −6° C. to about −3° C., for about 20 to about 40 minutes, preferably about 30 minutes. The mixture is stirred at about −50° C. to about −85° C., preferably about −78° C., for about 20 to about 40 minutes, preferably about 30 minutes, then treated with compound VI, at about −50° C. to about −85° C., preferably about −78° C., for about 20 to about 40 minutes, preferably about 30 minutes. The mixture is stirred at about −10° C. to about 5° C., preferably about 0° C. for about 30 to about 90 minutes, preferably about 60 minutes, then quenched with an aqueous pH 7 buffer solution, e.g., an aqueous solution of KH$_2$PO$_4$ and NaOH, and treated with methanol, and hydrogen peroxide, preferably 30% hydrogen peroxide, at about −5° C. to about 5° C., preferably about 0° C., for about 1 hour. The product is isolated by extraction and recrystallized from a suitable solvent, e.g., hexane/ethyl acetate, to obtain compound VII.

Alternatively, step A3 comprises treating compound V with titanium tetrachloride (TiCl$_4$), in a suitable inert organic solvent, e.g. CH$_2$Cl$_2$, at about −60° C., to about 0° C., preferably about −25° C. to about −15° C., and most preferably at about −20° C., for a period of about 10 minutes. Tetramethylethylenediamine (TMEDA) or a combination of TMEDA and triethylamine is added slowly over a period of about 10 minutes, while maintaining the temperature at about −25° C. to about −10° C. The mixture is stirred at about −25° C., to about −10° C., preferably about −15° C. to about −10° C., for a period of 30 to 90 minutes, preferably about 60 minutes, then treated with a compound of the formula VI The mixture is stirred at about −25° C., to about −10° C., preferably about −15° C. to about −10° C., for a period of 30 to 90 minutes, preferably about 60 minutes, then stirred for 30 to 60 minutes, preferably about 40 minutes, while warming to about 0° C. to about 10° C., preferably about 10° C. The mixture is quenched with an aqueous solution of tartaric acid, preferably a solution of about 10% tartaric acid in water. The product is then isolated by extraction with a suitable solvent, e.g. ethyl acetate, and recrystallized from a suitable solvent, such as ethyl acetate/hexane, to obtain compound VII.

In step A4, compound VII is treated with hydrogen peroxide, preferably 30% hydrogen peroxide, in a inert organic solvent, e.g., THF/water, at about −5° C. to about 5° C., preferably about 0° C., for about 10 to about 20 minutes, preferably about 15 minutes, then treated with a base, e.g., lithium hydroxide, at about −5° C. to about 5° C., preferably about 0° C., until no starting material remains, as determined by thin layer chromatography (TLC), in about 2 hours to about 4 hours, preferably about 3 hours. The excess peroxide is reduced by slowly adding a solution of sodium sulfite in water to the mixture over a period of about 30 to about 90 minutes, preferably about 70 minutes. The bulk of the solvent is removed under vacuum and the residue diluted with water. The chiral auxillary is recovered from the mixture by extraction with a suitable inert organic solvent, e.g., toluene. The remaining aqueous solution is acidified to a pH of about 2.0 to about 3.0, preferably pH of about 2.4, using hydrochloric acid. The product is isolated by extraction using a suitable inert organic solvent, e.g., ethyl acetate, to provide compound VIII.

In step A5, compound VIII is reacted with compound IX, a dehydrative coupling agent, e.g., dicyclohexylcarbodiimide (DCC), and an activating agent, e.g., 1-hydroxybenzotriazole (HOBT), in a suitable inert organic solvent, e.g., dimethylformamide or acetonitrile, at about 25° C. to about 50° C., preferably about 40° C. The reaction is continued until the starting material is consumed, as determined by TLC, in about 4 hours. The product is isolated by extraction to obtain compound X.

In step A6, compound X is cyclized by treating with triphenylphosphine or preferably a trialkylphosphine, e.g., tri-n-butylphosphine, and a dialkylazodicarboxylate, e.g., diethylazodicarboxylate (DEAD), in a suitable anhydrous organic solvent, e.g., dry THF, under a dry, inert atmosphere, e.g. nitrogen, at about −50° C. to about −85° C., preferably about −70° C., for about 1 to about 3 hours, preferably about 2 hours. The reaction is then continued at about room temperature for about 12 to about 24 hours. The product is purified by preparative high performance liquid chromatography (HPLC) to obtain a compound of formula I, having trans relative stereochemistry. The use of tributylphosphine in this step gives reaction yields significantly higher (a 128% increase) than the yields obtained using triphenylphosphine.

Alternatively, step A6 comprises combining compound X and a suitable phase transfer catalyst, e.g. tetra-n-butylammonium hydrogen sulfate, in a suitable solvent, such as methylene chloride. The mixture is stirred while cooling to about 0° C. to 20° C., preferably about 10° C. to about 20° C., then treated with an aqueous base, such as an alkali metal hydroxide, preferably 50% aqueous sodium hydroxide. A di- or tri-chlorobenzoyl chloride, preferably 2,6-dichlorobenzoyl chloride or 2,4,6-trichlorobenzoyl chloride, is slowly added over a period of 20 to 60 minutes, preferably about 30 minutes. The mixture is stirred at about 0° C. to about 25° C., preferably about 15° C. to about 20° C., for a period of 2 to 4 hours, preferably about 3 hours, then poured into cold water. The organic layer is separated and washed with water to neutral pH. The di-or trichlorobenzoate product is isolated by crystallization from methylene chloride/heptane. The di- or trichlorobenzoate product is combined with a suitable phase transfer catalyst, e.g. benzyltriethylammonium chloride, in a suitable solvent, such as a mixture methylene chloride and methyl t-butyl ether. The mixture is stirred at about 0° C. to about 25° C., preferably about 15° C. to about 20° C., and treated with an aqueous base, e.g. an alkali metal hydroxide, preferably 50% aqueous sodium hydroxide. After stirring for a period of 2 to 6 hours, preferably about 4 hours, the mixture is poured into ice water. The organic layer is washed with water to neutral pH. The product is isolated by removing the solvent, then purified by chromatography and recrystallization from a suitable solvent to give a compound of formula I, having trans relative stereochemistry.

A third alternative for step A6 comprises treating compound X in a suitable solvent, such as THF, DMF or $CH_2Cl_2$, with a dialkylchlorophosphate, preferably diethylchlorophosphate, and a metal hydride, preferably sodium hydride.

Another alternative for step A6 comprises treating compound X in a suitable solvent, such as $CH_2Cl_2$, with a dialkylchlorophosphate, preferably diethylchlorophosphate, and an aqueous base, such as an alkali metal hydroxide, preferably 50% aqueous sodium hydroxide, in the presence of a suitable amount, preferably a catalytic amount, of a phase transfer catalyst, such as tetra-n-butylammonium hydrogen sulfate or benzyltriethylammonium chloride.

Still another alternative for step A6 comprises treating compound X with a di- or tri-chlorobenzoyl chloride, preferably 2,6-dichlorobenzoyl chloride or 2,4,6-trichlorobenzoyl chloride, and a suitable base, such as sodium hydride in a suitable solvent, such as $CH_2Cl_2$, dimethylformamide, or a combination thereof. The product is isolated and purified by chromatography followed by crystallization from a suitable solvent, e.g. ether/hexane.

Starting compounds II, IV, VI, and IX are all either commercially available or well known in the art and can be prepared via known methods.

In another aspect (Method B), the process of this invention comprises converting the product obtained by condensing a chiral imide with a Schiff's base, i.e. an imine, to a β-lactam according to Reaction Scheme B.

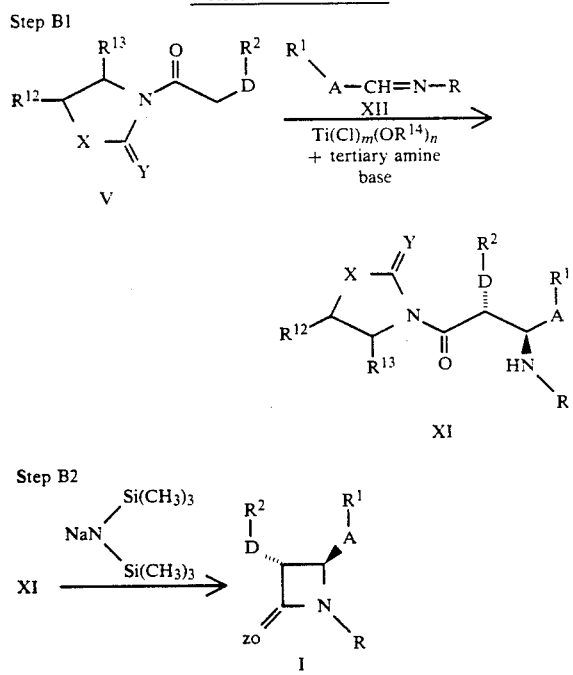

In step B1, compound V (from Method A, step 2), prepared from a chiral auxillary IV which is preferably S-4-phenyloxazolidinone, is dissolved in a suitable solvent, e.g. methylene chloride, then treated with a suitable Lewis acid, such as $TiCl(O-i-propyl)_3$ or $TiCl_4$, preferably $TiCl_4$, at about $-60°$ C. to about $0°$ C., preferably about $-25°$ C. to about $-15°$ C., under a dry, inert atmosphere, preferably nitrogen, for a period of about 5 min. A tertiary amine base, such as TMEDA, triethylamine or Hünig's base, preferably Hünig's base, is added and the mixture stirred at about $-60°$ C. to about $-10°$ C., preferably about $-25°$ C. to about $-20°$ C., for a period of about 1 hour. The imine XII is slowly added over a period of 20 to 40 min., preferably about 30 min., and the mixture is stirred at about $-60°$ C. to about $0°$ C., preferably about $-25°$ C. to about $-15°$ C., for 20 to 40 min., preferably about 30 min. The mixture is then warmed to about $0°$ C. and the reaction monitored by high pressure liquid chromatography (HPLC) until complete. The mixture is poured into a solution of tartaric acid in water, preferably 10% tartaric acid. The product XI is isolated by extraction with a suitable solvent, e.g. ethyl acetate, then purified by crystallization.

In step B2, the product of step B1 is treated with a strong non-nucleophilic base, such as sodium or lithium bistrimethylsilylamide or lithium diisopropylamide, preferably $NaN(Si(CH_3)_3)_2$, in a suitable inert organic solvent, e.g. $CH_2Cl_2$, at about $-20°$ C. to about $10°$ C., preferably about $0°$ C. The mixture is stirred while gradually warming to about $20°$ to about $25°$ C., then monitored by HPLC until the starting material is gone, typically after a period of 1 to 2 hours. The reaction mixture is poured into aqueous tartaric acid, preferably 10% tartaric acid, and the product I isolated from the organic layer.

Imines (XII) of the formula $R^1$—A—CH=N—R can be prepared from aldehydes VI and amines IX, as defined above, by procedures well known in the art.

It will also be apparent to those skilled in the art, and by reference to the examples which follow, that compounds of formula I can be converted into different compounds of formula I by well known methods. For example, a compound of formula I wherein A comprises a double or triple bond can be converted to the corresponding saturated compound by treatment with hydrogen gas in the presence of a catalyst such as palladium or platinum on carbon.

Reactive groups not involved in the above processes can be protected during the reactions with conventional protecting groups which can be removed by standard procedures after the reaction. The following Table 1 shows some typical protecting groups:

TABLE 1

| Group to be Protected | Group to be Protected and Protecting Group |
|---|---|
| —COOH | —COOalkyl, —COObenzyl, —COOphenyl |
| \>NH | \>NCOalkyl, \>NCObenzyl, \>NCOphenyl, |
| | \>NCH$_2$OCH$_2$CH$_2$Si(CH$_3$)$_3$, \>NC(O)OC(CH$_3$)$_3$, |
| | \>N-benzyl, \>NSi(CH$_3$)$_3$, \>NSi—C(CH$_3$)$_3$ with CH$_3$ groups |

TABLE 1-continued

| Group to be Protected | Group to be Protected and Protecting Group |
|---|---|
| —NH₂ | 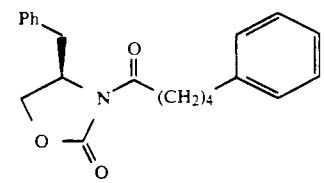 |
| —OH | —OCH₃, —OSi(CH₃)₃, —OSi—C(CH₃)₃ with CH₃/CH₃ |

The following examples illustrate the process of this invention:

EXAMPLE 1

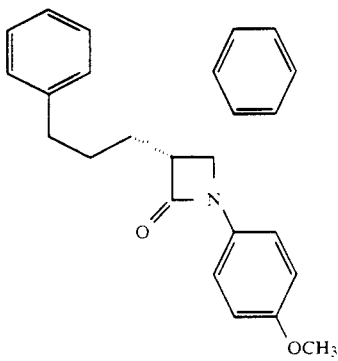

step (a)

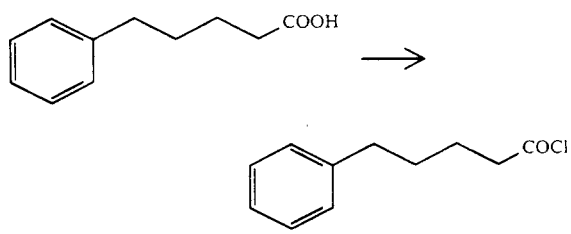

Combine 5-phenylvaleric acid (89.9 g, 0.504 mol) and thionyl chloride (89.3 mL, 1.225 mol) in a 500 mL round bottom flask equipped with a condenser and drying tube. Heat the flask to 70° C. and maintain the reaction at reflux for 1 h. Vacuum distill (50–100 mm Hg) the excess thionyl chloride and add 200 mL of dry toluene to the remaining mixture. Vacuum distill a second time to remove the toluene and any residual thionyl chloride. Add 188 mL of dry THF to the crude acid chloride remaining in the reaction vessel and use the resulting solution directly in the next step.

step (b)

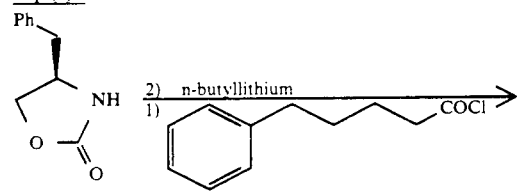

step (b)
-continued

Combine 76 g (0.4289 mol) of R-(+)-4-benzyloxazolidinone and 1.3 L of dry THF under dry nitrogen atmosphere. Cool the resulting solution to −78° C. and add 278 mL of a 1.6M solution of n-butyllithium in hexane over a period of 30–40 minutes. Stir the mixture for an additional 30 minutes following the addition. Add the solution of 5-phenylvaleroyl chloride from step (a) over a period of 45 minutes. Allow the mixture to warm to 0° C. and stir for 1 h. Quench the reaction mixture by adding 673.6 mL of K₂CO₃ (1M aqueous solution) and stir for 1 h. Distill off the THF under vacuum at 30°–35° C. Dilute the residue with 1 L of water and extract with three 800 mL portions of dichloromethane. Combine the organic extracts and wash with 800 mL of water, then with 800 mL of brine. Dry the organic extracts over MgSO₄, filter, then concentrate in vacuo to an oil. Dissolve the oil in 200 mL of hexane, then distill off the hexane under vacuum. Repeat the hexane treatment two more times, then dissolve the oil in 1.7 L of dichloromethane. The resulting solution is used directly in the next step.

Using substantially the same procedure, the following compound can be prepared:

1(b)-A

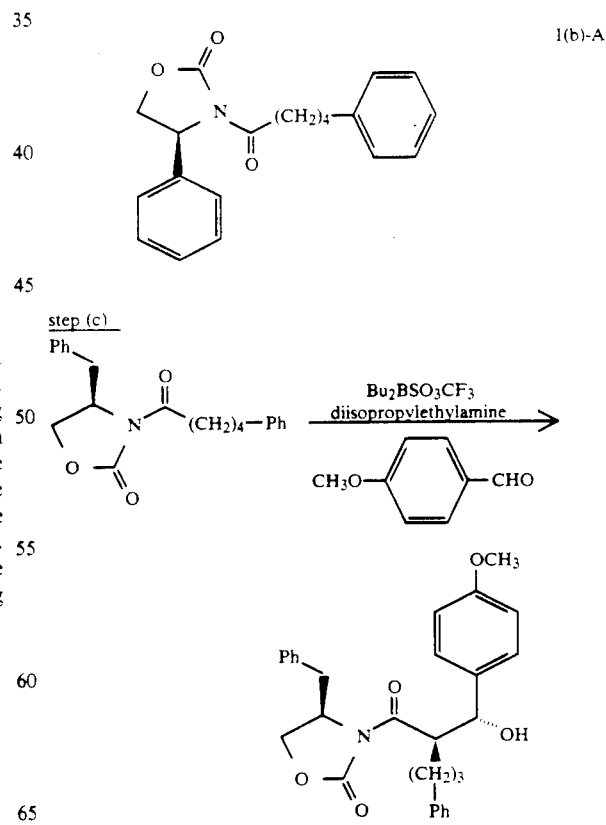

Cool the solution of the product from step (b) to −5° C. to 0° C., under dry nitrogen atmosphere. Add 130.0 mL of di-n-butylboron triflate at a rate that maintains the temperature of the reaction mixture at −6° C. to −3° C. Following the addition, stir the mixture for 10 minutes, then add 97.0 mL of diisopropylethylamine at a rate that maintains the temperature of the reaction mixture at −6° C. to −3° C. Following the addition, stir the mixture at 0° C. for 30 minutes, then cool the mixture to −78° C. and stir for 30 minutes. Add 57.4 mL of p-anisaldehyde and stir the mixture at −78° C. for 30 minutes, then at 0° C. for 1 h. While maintaining the temperature at 0° C. to 5° C., quench the mixture by adding 688 mL of a pH 7 buffer solution (68 g KH₂PO₄, 12 g NaOH and 800 mL of water), then add 473 mL of 30% H₂O₂ and stir the resulting mixture at 0° C. for 1 h. Extract the mixture with three 600 mL portions of hexane:ethyl actate (1:1). Combine the organic extracts and wash with 800 mL of saturated NaHCO₃ (aqueous), then with 800 mL of brine. Dry the organic extracts over NaSO₄, filter, and evaporate to an oil. Crystallize the oil from hexane/ethyl acetate (1:1) to give 176 g of the product as a white solid.

step (d)

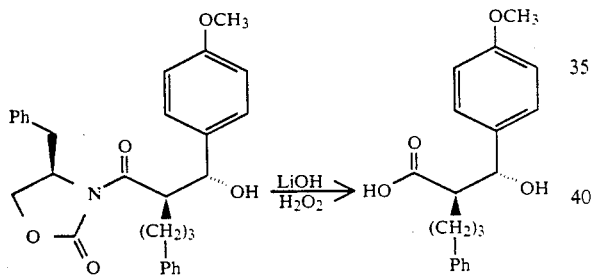

Combine the product of step (c) (170 g, 0.36 Mol), 1595 mL of THF and 400 mL of water, stir the mixture and cool to about 3° C. Add 226 mL (2.156 Mol) of 30% H₂O₂ to the mixture over 15 minutes, then add a solution of LiOH (36.2 g, 0.862 Mol) in 400 mL of water over a period of 30 minutes. Stir the reaction mixture at 0° C. to 5° C. for 3 h. Add a solution of 272 g of sodium sulfite in 850 mL of water over 70 minutes while keeping the temperature under 27° C. Distill off the bulk of the solvent under vacuum and add 7 L of water. Extract with four 1.7 L portions of toluene. (The toluene extracts contain R-(+)-4-benzyloxazolidinone which can be recovered and reused in Example 2.) Acidify the aqueous layers to pH 2.4 with 3N HCl. Extract with one 2.6 L portion and two 1.7 L portions of ethyl acetate. Combine the ethyl acetate extracts, wash with brine, dry over NaSO₄, filter, then evaporate to give the product as a white solid, 112 g.

step (e)

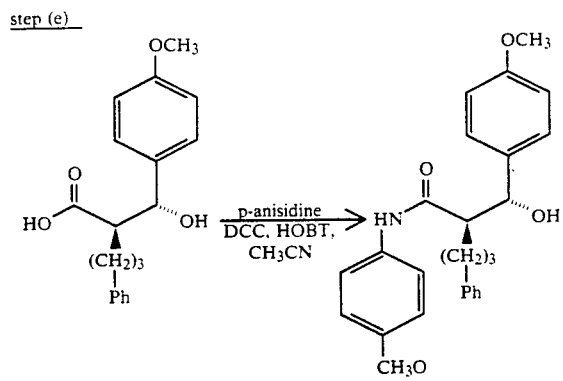

Combine the product of step (d) (19.47 g, 62 mmol), 400 mL of acetonitrile, 9.49 g (62 mmol) of 1-hydroxybenzotriazole (HOBT), 22.91 g (186 mmol) of p-anisidine and 14.05 g (68.2 mmol) of dicyclohexylcarbodiimide (DCC). Stir the reaction mixture at 40° C. for 4 h and confirm the consumption of starting material by TLC (6:4 hexane/ethyl acetate). Concentrate the mixture to 1/3 its volume and partition between 300 mL of water and 300 mL of ethyl acetate. Filter the organic layer, then wash with 200 mL of 1N HCl, then with two 100 mL portions of saturated NaHCO₃, and two 100 mL portions of brine. Dry the organic layer over NaSO₄ and concentrate to give the product as a brown solid, 24 g.

step (f)

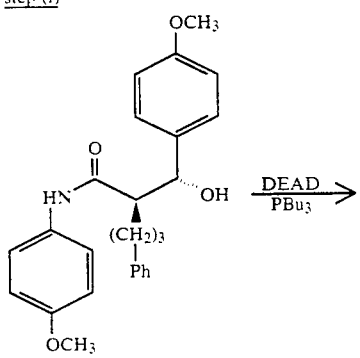

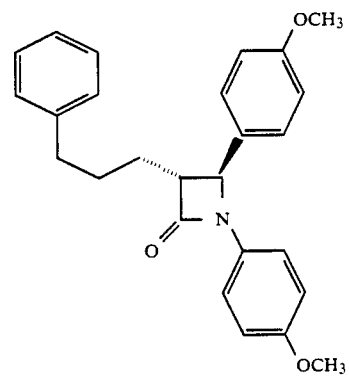

Combine the product of step (e) (115 g, 0.2745 Mol) and 2.3 L of THF under dry nitrogen atmosphere and cool to −70° C. Stir the mixture and simultaneously add: a solution of 137 mL (0.551 Mol) of tri-n-butylphosphine diluted in THF to a total volume of 163 mL;

and a solution of 87 mL (0.552 Mol) of diethylazodicarboxylate (DEAD) diluted to a total volume of 163 mL in THF, over 2 h. Allow the mixture to warm to room temperature and stir overnight. Remove the solvent under vacuum. Filter the residue through a plug of silica gel using dichloromethane/hexane/ethyl acetate (70:24:6) as the eluant. Evaporate the solvent and purify the residue by preparative HPLC (silica gel, 15% ethyl acetate/hexane) to give 88 g (80% yield) of the β-lactam product. When this reaction was carried out with triphenylphosphine the yield was only 30–35%.

Example 2

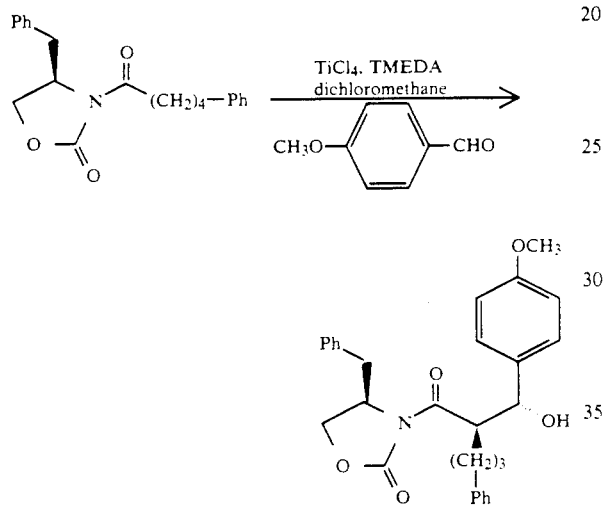

Cool a solution of 33.7 g (0.1 mol) of the product of Example 1, step (b), in 200 mL of CH₂Cl₂ to −20° C. Stir the cold solution and add 11 mL (0.1 mol) of TiCl₄. Stir the mixture for 10 min. at −20° C., then slowly add 30 mL (2 equiv.) of tetramethylethylenediamine (TMEDA) over a period of 10 min., while keeping the temperature below −10° C. Stir the mixture at −15° to −10° C. for 70 min., then add 24 mL (2 equiv.) of p-anisaldehyde. Stir at −15° to −10° C. for 1 hour, then allow the mixture to warm to 10° C. while stirring for 40 min. Quench the reaction by adding 600 mL of 10% aqueous tartaric acid, then add 600 mL of ethyl acetate. Agitate well, then separate the layers, extracting the aqueous layer with another 200 mL of ethyl acetate. Combine the organic extracts and wash successively with water, saturated NaHCO₃ (aqueous) and brine. Dry the organic solution over anhydrous Na₂SO₄, filter, then concentrate to a residue. Crystalline the residue from a mixture of 100 mL of ethyl acetate + 210 mL of hexane to give 36.8 g of the desired compound, which can be used in step (d) of Example 1.

EXAMPLE 3

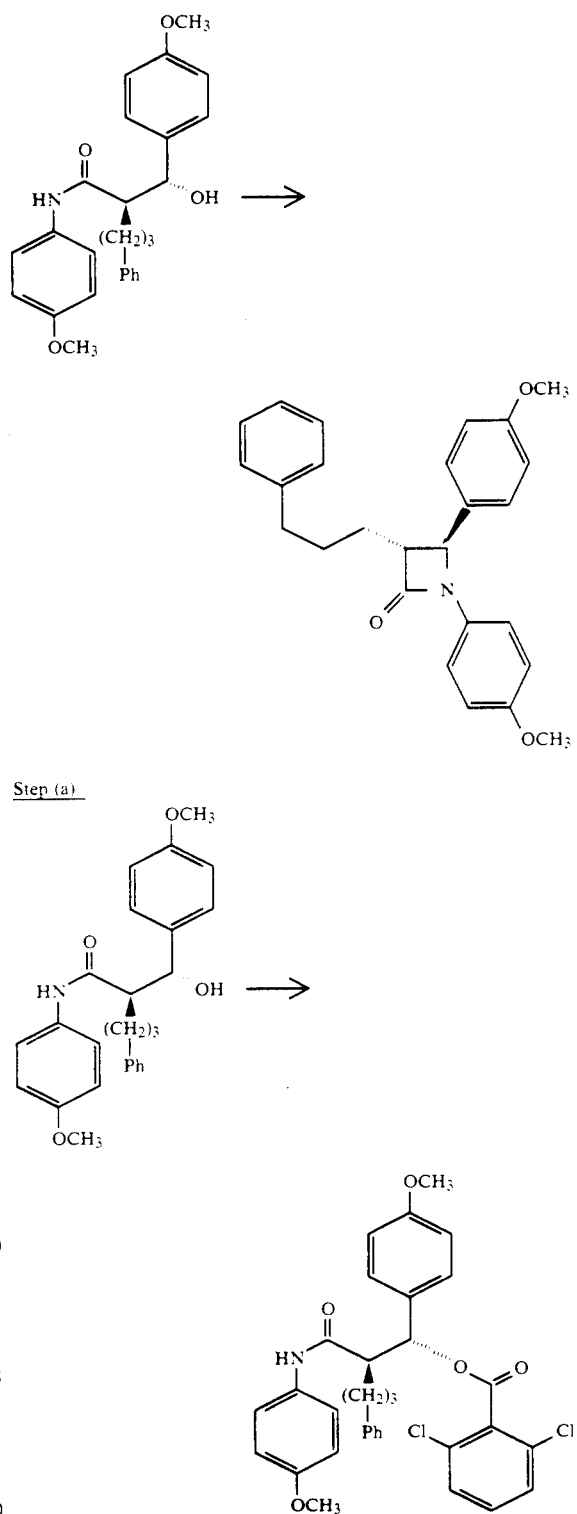

Dissolve 500 g (0.85 mol) of the product of Example 1, step (e), in 1700 mL of CH₂Cl₂, then add 4.0 g (12 mmol) of tera-n-butylammonium hydrogen sulfate. Stir the mixture while cooling to 10° to 20° C. and add 50% aqueous NaOH (200 g). Slowly add 60 g (285 mmol) of 2,6-dichlorobenzoyl chloride to the stirred mixture over a period of 30 min. Continue stirring at 15° to 20° C. for 3 h., then pour the mixture into 2000 mL of cold water. Separate the layers and wash the organic layer with water until neutral pH is attained. Distill the methylene chloride solution to reduce the volume to 800 mL. Heat the solution to reflux and add 800 mL of heptane. Cool the hot solution to 0° C. to crystallize. Collect the product by filtration to give 116 g of the dichlorobenzoate product.

Step (b)

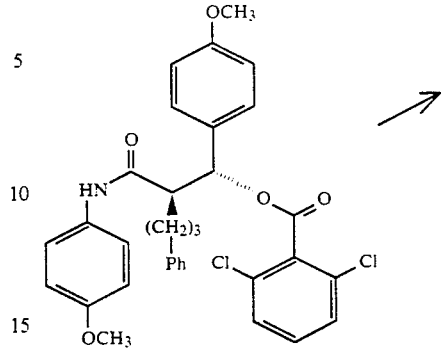

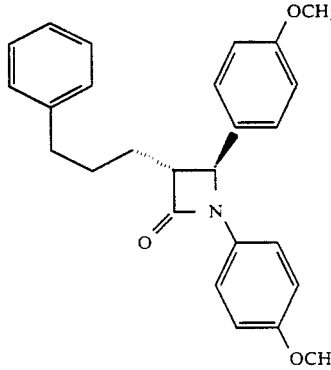

Combine 500 g (0.85 mol) of the product of step (a) with 250 g (1.1 mol) of benzyltriethylammonium chloride, 2000 mL of $CH_2Cl_2$ and 8000 mL of methyl t-butyl ether. Stir the mixture while cooling to 15° to 20° C., then add 1000 mL of 50% aqueous NaOH over a period of 10 min. Stir the mixture for 4 h., then pour into 5000 mL of water and 4 kg of ice. Separate the layers and wash the organic layer with water until the pH is neutral. Distill the solvent to reduce the volume to 2000 mL, then filter. Evaporate the filtrate to a residue and purify the residue by chromatography on silica gel to obtain the pure product. The product is obtained as a solid by crystallization from 6 volumes of a 1:2 mixture of methyl t-butyl ether and heptane at 0° C. to give the product (240 g).

EXAMPLE 4

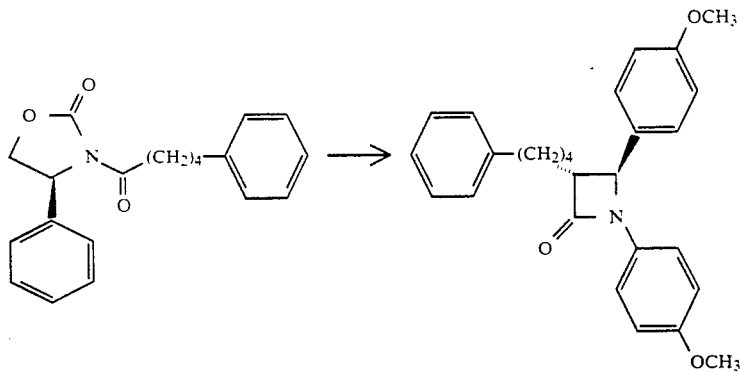

Step (a):

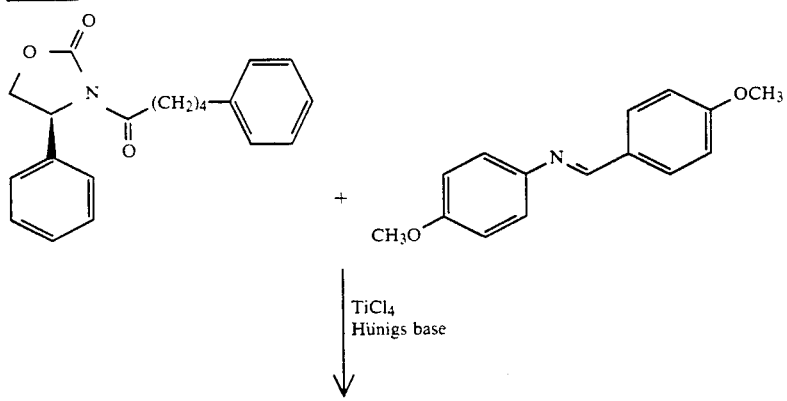

-continued

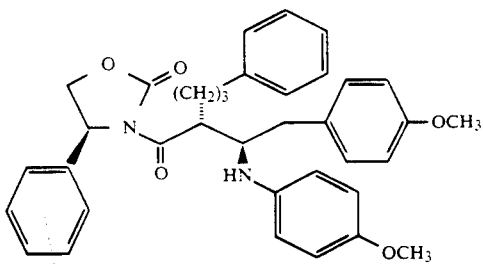

Dissolve 3.23 g (10 mmol) of the product of Example 1, step (b)-A, in 50 mL of CH₂Cl₂, then stir under nitrogen atmosphere while cooling to −20° C. Add 10 mL (10 mmol) of a 1M solution of TiCl₄ in CH₂Cl₂, stir the mixture for 5 min., then add 1.7 mL (10 mmol) of Hünig's base. Stir the mixture at −25° to −20° C. for 1 h., then slowly add 4.8 g (20 mmol) of the Schiff's base derived from anisaldehyde and p-anisidine as a solution in 50 mL of CH₂Cl₂ over a period of 30 min. Stir the mixture at −20° C. for 30 min. then gradually warm to 0° C. The reaction is monitored by HPLC (Zorbax® Sil column, 1:4 ethyl acetate/hexane), while stirring at 0° C., until complete. Quench the mixture by pouring into 50 mL of 10% aqueous tartaric acid. Extract with ethyl acetate, then wash the organic extract successively with saturated NaHCO₃ (aqueous) and brine. Dry the organic solution over anhydrous Na₂SO₄, filter, then concentrate to give the crude product. Crystallize from ethyl acetate/hexane to give the purified product.

Step (b):

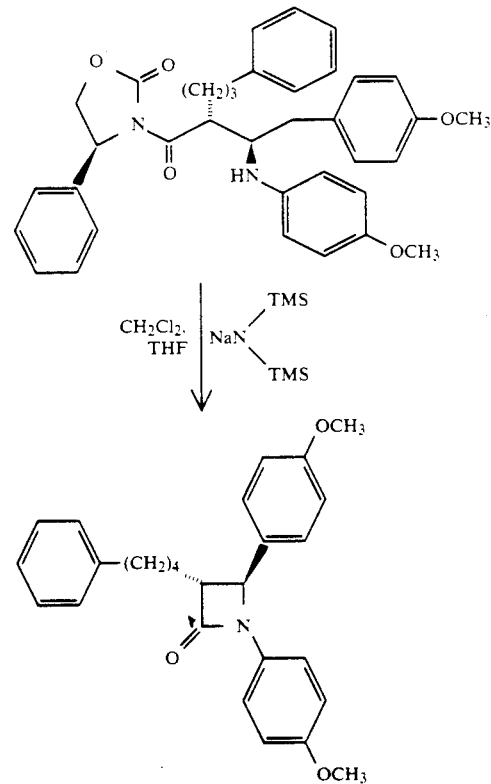

A solution of 0.505 g (0.89 mmol) of the product of step (a) in 25 mL of CH₂Cl₂ is stirred at 0° C., then treated with 1.77 mL (1.77 mmol) of a 1M solution of sodium bistrimethylsilylamide in THF. Stir the mixture while warming to room temperature, then continue stirring until the starting material is gone as determined by HPLC (typically 1 to 1½ h.) Quench the mixture into 10% tartaric acid (aqueous). Wash the organic layer successively with saturated NaHCO₃ (aqueous) and brine, then dry over anhydrous Na₂SO₄. Filter, concentrate and chromatograph (silica gel, 15% or 20% EtOAc/hexane) to give the title compound.

Example 5

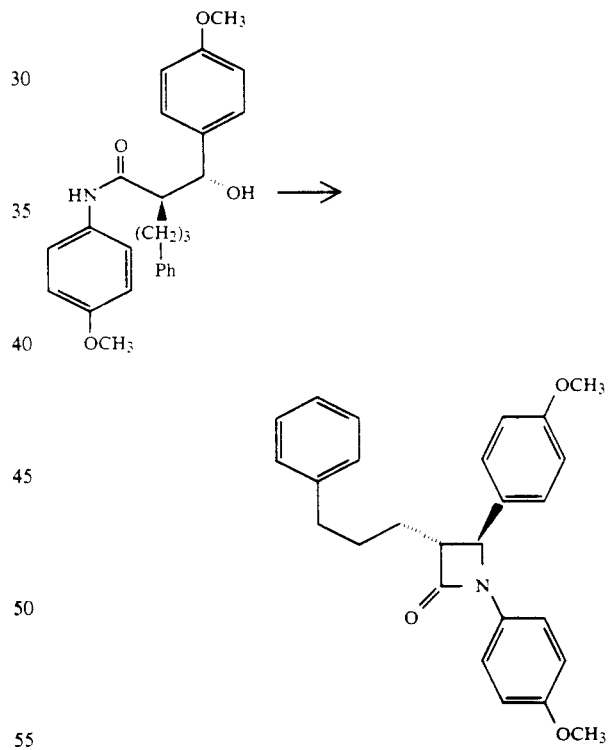

Dissolve 5 g (11.1 mmol) of the product of Example 1, step (e), in 240 mL of 5:1 CH₂Cl₂/DMF, cool to 0° C. and add 1.7 mL (11.86 mmol) of 2,6-dichlorobenzoyl chloride. Carefully add 1-1.2 g of NaH (60% suspension in oil) and continue stirring while allowing the mixture to warm from 0° C. to room temperature. Continue stirring until the reaction is complete (6-12 h.) as determined by HPLC or thin layer chromatography (TLC). Quench any excess NaH by adding a dilute solution of acetic acid in CH₂Cl₂. Dilute the mixture with 200-300 mL of water, separate the layers and extract the aqueous layer with 50 mL of CH₂Cl₂. Combine the extract and the original organic layer and wash with saturated NaHCO3 (aqueous), and then with brine. (The 2,6-dichlorobenzoic acid can be recovered from the NaHCO3 wash.) Dry over Na2SO4, filter, and concentrate to give a residue. Chromatograph the residue (silica gel, 15% EtOAc/hexane), then crystallize from Et2O/hexane to obtain 2.7 g (61% yield) of the title compound.

Example 6

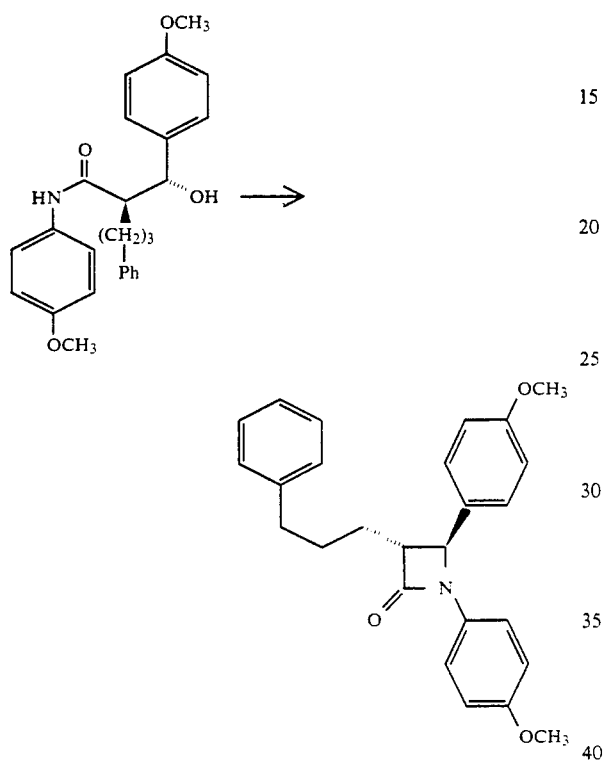

Combine 100 g (239 mmol) of the product of Example 1, step (e), 1.0 g (4.4 mmol) of benzyltriethylammonium chloride and 1000 mL of CH2Cl2 and cool the mixture to 10° C. While maintaining the mixture at 10°–15° C., add 500 mL of 50% NaOH (aqueous). With the mixture at 10°–15° C., stir while adding 53 mL (359 mmol) of diethylchlorophosphate, dropwise, over a period of 15 min. Continue stirring at 10°–15° C. for 4 h., at which time the reaction is complete by HPLC. Quench the mixture into 1000 mL of ice-cold water, using an additional 500 mL of ice water and 300 mL of CH2Cl2 to aid in the transfer. Separate the layers and wash the organic layer with 10% brine solution (4×500 mL). Extract the combined aqueous solutions with 500 mL of CH2Cl2, and wash this extract with 10% brine (4×200 mL). Combine the organic solutions, dry over MgSO4 and concentrate to a residue. Dissolve the residue in toluene and pass the solution through a column of silica gel (100 g) using toluene to elute. Concentrate to a residue, dissolve the residue in 300 mL of heptane, evaporate, and repeat the process with an additional 300 mL of heptane. Crystallize the resulting residue from methyl tert-butyl ether/isopropanol to give 62 g of the title compound.

We claim:

1. A process for producing a chiral compound of the formula

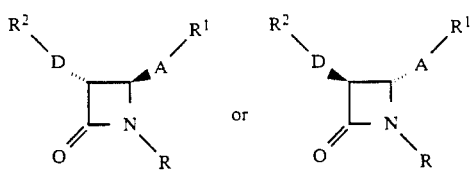

wherein
R is phenyl, W-substituted phenyl, naphthyl, W-substituted naphthyl, benzodioxolyl, heteroaryl, W-substituted heteroaryl, benzofused heteroaryl and W-substituted benzofused heteroaryl, wherein heteroaryl is selected from the group consisting of pyrrolyl, pyridinyl, pyrimidinyl, pyrazinyl, triazinyl, imidazolyl, thiazolyl, pyrazolyl, thienyl, oxazolyl and furanyl, and for nitrogen-containing heteroaryls, the N-oxides thereof;
$R^1$ and $R^2$ are independently selected from H or R;
W is 1 to 3 substituents independently selected from the group consisting of lower alkyl, hydroxy lower alkyl, lower alkoxy, alkoxyalkyl, alkoxyalkoxy, alkoxycarbonylalkoxy, (lower alkoxyimino)-lower alkyl, lower alkanedioyl, lower alkyl lower alkanedioyl, allyloxy,
—$CF_3$, —$OCF_3$, benzyl, $R^3$-benzyl, benzyloxy, $R^3$-benzyloxy, phenoxy, $R^3$-phenoxy, dioxolanyl, $NO_2$, —$NR^4R^5$, $NR^4R^5$ (lower alkyl)-, $NR^4R^5$(lower alkoxy)-, OH, halogeno, —NHC(O)$R^6$, —NHC(O)$R^6$, $R^7O_2SNH$-, ($R^7O_2S$)$_2N$—, —$S(O)_2NH_2$, —$S(O)_{0-2}R^4$, tert-butyldimethyl-silyloxymethyl, —$C(O)R^8$,

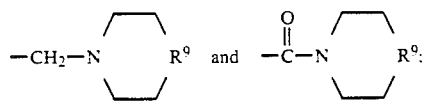

A and D are independently a bond; $C_3$–$C_6$ cycloalkylene; $C_1$–$C_{10}$ alkylene; $C_1$–$C_{10}$ alkenylene; $C_1$–$C_{10}$ alkynylene; an alkylene, alkenylene or alkynylene chain as defined substituted by one or more substituents independently selected from the group consisting of phenyl, W-substituted phenyl, heteroaryl and W-substituted heteroaryl, wherein heteroaryl is as defined above; an alkylene, alkenylene or alkynylene chain as defined interrupted by one or more groups independently selected from the group consisting of —O—, —S—, —SO—, —$SO_2$—, —$NR_8$, —C(O)—, $C_3$–$C_6$ cycloalkylene, phenylene, W-substituted phenylene, heteroarylene and W-substituted heteroarylene; or an interrupted alkylene, alkenylene or alkynylene chain as defined substituted by one or more substituents independently selected from the group consisting of phenyl, W-substituted phenyl, heteroaryl and W-substituted heteroaryl; or $R^2$-D is selected from the group consisting of halogeno, OH, lower alkoxy, —OC(O)$R^6$, —$NR^4R^5$, —SH and —S(lower alkyl);
$R^3$ is 1-3 groups independently selected from the group consisting of lower alkyl, lower alkoxy, —COOH, $NO_2$, —$NR^4R^5$, OH or halogeno;
$R^4$ and $R^5$ are independently selected from H and lower alkyl;
$R^6$ is lower alkyl, phenyl, $R^3$-phenyl, benzyl or $R^3$-benzyl;

R[7] is OH, lower alkyl, phenyl, benzyl, R[3]-phenyl or R[3]-benzyl;

R[8] is H, OH, alkoxy, phenoxy, benzyloxy,

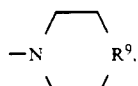

—NR[4]R[5], lower alkyl, phenyl or R[3]-phenyl;

R[9] is —O—, —CH$_2$—, —NH— or —N(lower alkyl)—;

R[10] is H, lower alkyl, phenyl lower alkyl or —C(O)R[11];

R[11] is H, lower alkyl, phenyl or phenyl lower alkyl;

provided that when A is a bond, R[1] is not H, and provided that when R[1] is W-substituted phenyl, W is not p-halogeno;

comprising cyclizing a hydroxyamide of the formula

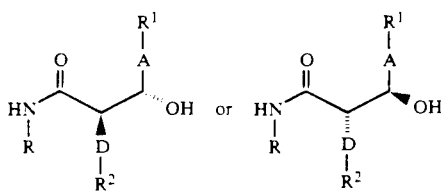

wherein D, A, R[1], R[2] and R are as defined above, by treating with: a dialkylchlorophosphate and either a metal hydride, or an aqueous solution of a base and a phase transfer catalyst.

2. A process according to claim 1, wherein the dialkylchlorophosphate is diethylchlorophosphate, the metal hydride is sodium hydride, the base is 50% aqueous sodium hydroxide and the phase transfer catalyst is tetra-n-butylammonium hydrogen sulfate or benzyltriethylammonium chloride.

3. A process for producing a chiral compound of the formula

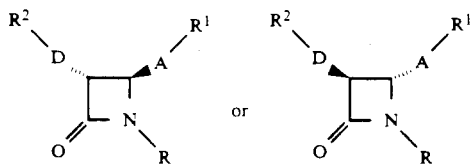

wherein R, R[1], R[2], D and A are as defined in claim 1, comprising:

(a) reacting a carboxylic acid of the formula R[2]-D-CH$_2$-COOH, wherein R[2] is as defined above, with a chlorinating agent;

(b) deprotonating a chiral auxillary of the formula

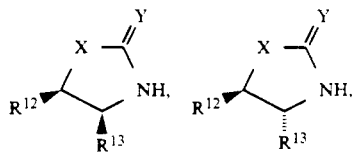

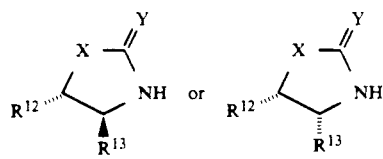

wherein X and Y are independently O or S, and R[12] and R[13] are independently selected from the group consisting of C$_1$-C$_6$ alkyl, phenyl, naphthyl, W-substituted phenyl, W-substituted naphthyl, lower alkoxycarbonyl and benzyl; or wherein one of R[12] or R[13] is as defined above and the other is hydrogen; and wherein W is as defined above; with a strong base and treating the resulting anion with the product of step (a);

(c) enolizing the product of step (b) with:
(i) a dialkylboron triflate and a tertiary amine base; or
(ii) TiCl$_4$ and a tertiary amine base selected from: tetramethylethylenediamine (TMEDA); triethylamine; or
a mixture of TMEDA and triethylamine; then condensing with an aldehyde of the formula R[1]-A-CHO, wherein R[1] and A are as defined above;

(d) hydrolyzing the product of step (c) with a base and hydrogen peroxide;

(e) condensing the product of step (d) with an amine of the formula RNH$_2$, wherein R is as defined above, by treating with a dehydrative coupling agent, optionally adding an activating agent; and (f) cyclizing the product of step (e) by reacting the product of step (e) with: a dialkylchlorophosphate and either a metal hydride, or an aqueous solution of a base and a phase transfer catalyst.

4. A process according to claim 3, wherein the chlorinating agent of step (a) is thionyl chloride, the strong base of step (b) is n-butyllithium, the dialkylboron triflate of step (c) is di-n-butylboron triflate, the base of step (d) is lithium hydroxide, the dehydrative coupling agent of step (e) is dicyclohexylcarbodiimide, and the activating agent of step (e) is 1-hydroxybenzotriazole.

5. A process according to claim 4, wherein the dialkylchlorophosphate of step (f)(iv) is diethylchlorophosphate, the metal hydride of step (f)(iv) is sodium hydride, the base of step (f)(iv) is 50% aqueous sodium hydroxide and the phase transfer catalyst of step (f)(iv) is tetra-n-butylammonium hydrogen sulfate or benzyltriethylammonium chloride.

6. A process according to claim 5, wherein the phase transfer catalyst is present in a catalytic amount.

7. A process according to claim 4, wherein the chiral auxillary of step (b) is R-(+)-4-benzyloxazolidinone, R[2]-D-CH$_2$COOH is 5-phenylvaleric acid, R[1]-A-CHO is p-anisaldehyde, and RNH$_2$ is p-anisidine.

* * * * *